(12) United States Patent
Steward et al.

(10) Patent No.: US 9,833,532 B1
(45) Date of Patent: *Dec. 5, 2017

(54) FRAGRANCE COMPOSITIONS CONTAINING LOW VAPOR PRESSURE VOC SOLVENTS

(71) Applicant: TAKASAGO INTERNATIONAL CORPORATION, Tokyo (JP)

(72) Inventors: Charles C. Steward, Rockleigh, NJ (US); Lambert Dekker, Rockleigh, NJ (US); Henry Van Den Heuvel, Rockleigh, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,988

(22) Filed: Aug. 18, 2016

Related U.S. Application Data

(63) Continuation of application No. 14/084,981, filed on Nov. 20, 2013, now Pat. No. 9,446,161, which is a continuation of application No. 12/717,078, filed on Mar. 3, 2010, now Pat. No. 8,603,963.

(60) Provisional application No. 61/157,181, filed on Mar. 3, 2009.

(51) Int. Cl.
*A61L 9/03* (2006.01)
*A61L 9/04* (2006.01)
*C11B 9/00* (2006.01)

(52) U.S. Cl.
CPC .............. *A61L 9/044* (2013.01); *C11B 9/008* (2013.01); *C11B 9/0015* (2013.01); *C11B 9/0019* (2013.01); *C11B 9/0046* (2013.01); *C11B 9/0061* (2013.01); *C11B 9/0076* (2013.01)

(58) Field of Classification Search
CPC ... A61L 9/03; A61L 9/12; A61L 9/044; A61L 9/127; A61Q 13/00
USPC .................. 512/2, 3, 25, 26; 239/34, 44
See application file for complete search history.

(56) References Cited

U.S. PATENT DOCUMENTS

| | | | | |
|---|---|---|---|---|
| 4,260,110 A * | 4/1981 | Werding | ............... | B05B 1/3436 239/404 |
| 5,160,494 A | 11/1992 | Krzysik et al. | | |
| 6,491,728 B2 | 12/2002 | Bacon et al. | | |
| 6,617,483 B1 * | 9/2003 | McKim | ............... | C07C 7/08 585/833 |
| 6,783,117 B2 * | 8/2004 | Wohrle | ............... | A61L 9/035 261/104 |
| 6,869,923 B1 | 3/2005 | Cunningham et al. | | |
| 7,481,380 B2 | 1/2009 | Kvietok et al. | | |
| 8,170,405 B2 * | 5/2012 | Harris | ............... | A01M 1/2033 392/386 |
| 8,603,963 B1 * | 12/2013 | Steward | ............... | A61L 9/03 239/34 |
| 9,446,161 B1 * | 9/2016 | Steward | ............... | A61L 9/03 |
| 2002/0158351 A1 * | 10/2002 | Wohrle | ............... | A61L 9/035 261/142 |
| 2003/0024997 A1 * | 2/2003 | Welch | ............... | A61L 9/01 239/53 |
| 2004/0116325 A1 * | 6/2004 | Goodacre | ............... | C11D 3/50 512/10 |
| 2004/0144406 A1 * | 7/2004 | Garabedian | ............... | A47L 13/12 134/26 |
| 2005/0214386 A1 * | 9/2005 | Shaheen | ............... | A61K 33/20 424/661 |
| 2005/0217698 A1 * | 10/2005 | Mitchell | ............... | A47L 13/20 134/6 |
| 2005/0250668 A1 * | 11/2005 | Serobian | ............... | C09G 1/16 510/466 |
| 2006/0276356 A1 * | 12/2006 | Panandiker | ............... | C11D 3/505 510/100 |
| 2007/0176015 A1 | 8/2007 | Farrell et al. | | |
| 2007/0191253 A1 * | 8/2007 | Kilkenny | ............... | A01N 37/36 510/424 |
| 2008/0193387 A1 | 8/2008 | De Wolff et al. | | |
| 2008/0308648 A1 | 12/2008 | Pesu | | |
| 2009/0022682 A1 | 1/2009 | Licciardello | | |
| 2009/0117069 A1 * | 5/2009 | Mainz | ............... | A61L 9/05 424/76.4 |
| 2009/0148342 A1 * | 6/2009 | Bromberg | ............... | A01N 59/00 422/37 |

FOREIGN PATENT DOCUMENTS

| | | |
|---|---|---|
| CA | 2662806 | 7/2009 |
| CA | 2662816 | 7/2009 |

OTHER PUBLICATIONS

U.S. Appl. No. 12/717,078, filed Mar. 3, 2010.
U.S. Appl. No. 14/084,981, filed Nov. 20, 2013.
U.S. Appl. No. 14/084,981, Aug. 18, 2016 Issue Fee Payment.
U.S. Appl. No. 14/084,981, May 18, 2016 Notice of Allowance.
U.S. Appl. No. 14/084,981, May 3, 2016 Response after Final Action.
U.S. Appl. No. 14/084,981, Feb. 4, 2016 Final Office Action.
U.S. Appl. No. 14/084,981, Nov. 24, 2015 Response to Non-Final Office Action.
U.S. Appl. No. 14/084,981, Aug. 27, 2015 Non-Final Office Action.

(Continued)

Primary Examiner — Douglas McGinty
(74) Attorney, Agent, or Firm — Baker Botts L.L.P.

(57) ABSTRACT

A fragrance composition comprising a low vapor pressure VOC and at least one low vapor pressure VOC potentiator compound, which reduces, or altogether completely obviates the use of HVPVOC solvents in fragrance compositions.

11 Claims, 3 Drawing Sheets

(56) References Cited

OTHER PUBLICATIONS

U.S. Appl. No. 12/717,078, Nov. 7, 2013 Issue Fee payment.
U.S. Appl. No. 12/717,078, Aug. 7, 2013 Notice of Allowance.
U.S. Appl. No. 12/717,078, Jul. 29, 2013 Applicant Interview Summary.
U.S. Appl. No. 12/717,078, May 22, 2013 Non-Final Office Action.
U.S. Appl. No. 12/717,078, May 2, 2013 Amendment and Request for Continued Examination (RCE).
U.S. Appl. No. 12/717,078, Nov. 2, 2012 Final Office Action.
U.S. Appl. No. 12/717,078, Oct. 18, 2012 Supplemental Response.
U.S. Appl. No. 12/717,078, Aug. 2, 2012 Response to Non-Final Office Action.
U.S. Appl. No. 12/717,078, May 3, 2012 Non-Final Office Action.
U.S. Appl. No. 12/707,078, Jan. 9, 2012 Response to Non-Final Office Action.
U.S. Appl. No. 12/717,078, Oct. 7, 2011 Non-Final Office Action.
"A hydrophilic glyocol either with a moderate evaporation rate and tailing solvent activities," Dowanol DPMA, Mar. 2004; pp. 1-2.

* cited by examiner

FRAGRANCE COMPOSITIONS CONTAINING LOW VAPOR PRESSURE VOC SOLVENTS

CROSS REFERENCE TO RELATED APPLICATIONS

The present application is a continuation of U.S. patent application Ser. No. 14/084,981, filed Nov. 20, 2013, which issued as U.S. Pat. No. 9,446,161 on Sep. 20, 2016; which is a continuation of U.S. patent application Ser. No. 12/717,078, filed Mar. 3, 2010, which issued as U.S. Pat. No. 8,603,963 on Dec. 10, 2013; which claims the priority under 35 U.S.C. §119 to U.S. Provisional Application Ser. No. 61/157,181, filed Mar. 3, 2009, each of which is hereby incorporated by reference in their entireties, and from which priority is claimed.

FIELD OF THE INVENTION

The present invention relates to fragrance compositions containing low vapor pressure VOC (volatile organic compound) solvents.

BACKGROUND OF THE INVENTION

A problem in the area of air care devices is the uncontrolled "distillation" of fragrance components of differing volatilities, resulting in a variable fragrance profile over time, as perceived by the consumer. The use of carriers or solvents in fragrances aids in the uniform distribution or evaporation of these fragrance components and leads to a more homogeneous fragrance profile.

Many materials are used as carriers in air care devices including glycol ethers, isoparaffinic solvents (e.g., Isopar® solvents commercially available from ExxonMobil) and various branched esters. One problem associated with these materials is that many are classified as VOCs (volatile organic compounds). VOC's are increasingly of environmental and regulatory concern. There is one class of VOCs, low vapor pressure VOC's (LVPVOCs), that are not as harmful to the atmosphere and are generally allowed under even the most stringent environmental regulations. This class of VOC has lower vapor pressure than regular VOCs as defined by standard definitions (e.g., <0.1 mm Hg at 20° C.).

U.S. Published Application No. 2008/0308648 discloses, in the generic sense, fragrance compositions containing Dowanol DPMA for use in a non-electric, wick-type device. DPMA has not, heretofor, been widely used as a fragrance carrier in liquid electrical air freshener devices, if used at all. The low volatility of low vapor pressure VOCs, such as DPMA, presents unique challenges. The decreased vapor pressure changes the compositions' perceived fragrance profile, as compared to the same fragrance composition used with a high vapor pressure VOC solvent (HVPVOC solvent).

There is a need for hedonically pleasing fragrance compositions that can be combined with low vapor pressure VOC solvents, such as dipropylene glycol methyl ether acetate. For example, there is a need for fragrance compositions that can be combined with a low vapor pressure VOC carrier for use in a liquid electrical air freshener, such as a heated wick delivery system, a piezoelectrical spraying system, an electrospray device or a Venturi device. It is desired to provide fragrance compositions suitable for use in air fresheners that avoid the regulatory problems associated with many of the glycol ether compounds commonly found in liquid electrical air fresheners. It is also desired to provide compositions that include a low pressure VOC (e.g., DPMA) and a fragrance composition wherein the evaporation rate is regulated to within a predetermined period of time (e.g., 30 days, or 40 days, or 60 days), during which at least substantially all of the fragrance is effectively evaporated into the surrounding environment, preferably in a controlled fashion.

It is thus an object to provide compositions that include one or more low pressure VOC (e.g., DPMA) and one or more a fragrance components that are economical to produce and have good safety characteristics, including low toxicity and low flammability.

Another and related object of the invention is to provide fragrance compositions that include a low pressure VOC (e.g., DPMA) and a fragrance composition having a controllable evaporation rate and that are suitable for use in, for example, a wick type air fragrance dispenser (air freshener). More specifically, it is an object of the invention to provide a controllable evaporation rate and permit effective utilization of the fragrance in a liquid electrical air freshener dispenser.

SUMMARY OF THE INVENTION

The presently disclosed subject matter provides specifically designed fragrance components that can be used in combination with low vapor pressure VOCs (e.g., DPMA). Surprisingly, it has been found that the use of one or more low vapor pressure VOCs, particularly DPMA, and specially constructed fragrance components that include at least one low vapor pressure VOC potentiator compound can maintain the volatility so that the composition performs properly in a electrical liquid air freshener device.

One aspect of the presently disclosed subject matter provides a fragrance composition that includes a low vapor pressure VOC (e.g., dipropylene glycol methyl ether acetate) and at least one low vapor pressure VOC potentiator compound. In one embodiment, the fragrance composition contains at least 10 wt %, or at least 15 wt %, or at least 20 wt %, or at least 30 wt % of VOC potentiator compounds, based on the total weight of the fragrance composition. In an alternative embodiment, the fragrance composition contains at least 10 wt %, or at least 20 wt % of the least one low vapor pressure VOC, based on the total weight of the fragrance composition.

In one embodiment, at least one low vapor pressure VOC potentiator compound present in the fragrance composition has a vapor pressure, at 25° C., of at least about 0.2 mmHg, or at least about 0.5 mmHg, or at least 1 mmHg, and/or a flash point from about 110° F. to about 200° F., or from about 130° F. to about 180° F.

In one embodiment, one or more VOC potentiator compound(s) are represented by the formula:

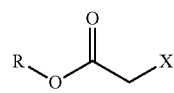

wherein
R is a $C_1$-$C_{10}$ substituted or unsubstituted alkyl, alkenyl group, or a $C_4$-$C_8$ substituted or unsubstituted cycloalkyl or aryl group; and
X is hydrogen, or a $C_1$-$C_5$ unsubstituted alkyl group.

In one embodiment, R is a $C_4$-$C_8$ substituted or unsubstituted alkyl group. In one embodiment, R is a $C_6$ substituted or unsubstituted alkyl group. R can be substituted, for example, anywhere along the chain with one or more methyl groups. In one embodiment, X is H. In one embodiment, X is $C_1$-$C_3$ unsubstituted alkyl group.

In one embodiment, the low vapor pressure VOC potentiator compound is selected from hexyl acetate, 3,3,5-trimethylhexyl acetate, bornyl formate, 3-hexenyl butyrate, phenyl ethyl acetal, butyl hexanoate, isononanol, acetone alcohol, isoprenyl acetate, isobutyl 2-pentanoate, amyl propionate, herbal dioxane, furfuryl formate, methyl acetyl acetone, and butyl acetoacetate. In one embodiment, the low vapor pressure VOC potentiator compound is selected from 3,3,5-trimethylhexyl acetate and hexyl acetate.

In one embodiment, at least 80%, or at least 90% of the fragrance composition, by weight, evaporates within 30 days, or 60 days, of being maintained at ambient conditions. Preferably, the fragrance composition evaporates in a controlled fashion. The evaporation rate can be tailored by a perfumer to suit the evaporation rate desired in the particular application.

A second aspect of the presently disclosed subject matter provides a fragrance consumer product (e.g., a electrical liquid air freshener device) that contains any one of the fragrance compositions disclosed herein.

A third aspect of the presently disclosed subject matter provides a method of decreasing the amount of high vapor pressure VOC solvent in a fragrance composition. This method includes removing at least a portion of any high vapor pressure VOC present in the composition (preferably the entire amount of high vapor pressure VOC present), adding at least one low vapor pressure VOC to the composition; and adding at least one low vapor pressure VOC potentiator compound to the composition to provide a low VOC solvent fragrance composition.

BRIEF DESCRIPTION OF THE DRAWINGS

For a more complete understanding of various embodiments of the described subject matter and its advantages, reference is now made to the following description, taken in conjunction with the accompanying drawings, in which.

DETAILED DESCRIPTION

Figure 1:
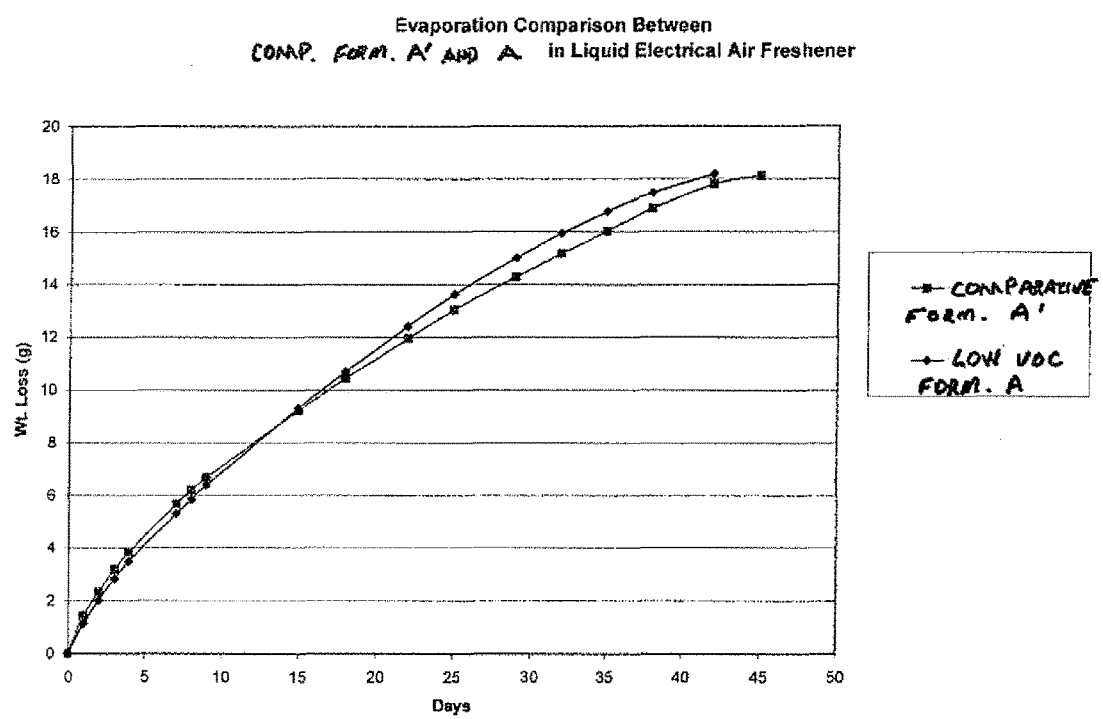
FIG. 1 is an evaporation comparison between the standard fragrance formulation A', and the Low Vapor Pressure VOC formulation A, as described in Example 1, measured as the amount of weight loss of fragrance over 40 days.

As used herein, a "low vapor pressure VOC" or "LVPVOC" refers to organic solvents or carriers for use in a consumer product containing fragrance materials that have a vapor pressure of less than (<) 0.1 mm Hg at 20° C.

As used herein, a "high vapor pressure VOC" or "HVPVOC" refers to organic solvents or carriers for use in a consumer product containing fragrance materials that have a vapor pressure greater than or equal to (≥) 0.1 mm Hg at 20° C.

As used herein, the term "solvent" and "carrier" are used interchangeably and, unless specified otherwise, are generally mentioned with respect to a low vapor pressure VOC or high vapor pressure VOC.

As used herein, the phrase "consumer product" or "end product" refers to composition that is in a form ready for use by the consumer for a marketed indication.

As used herein, a "solvent suitable for use in a consumer product" is a solvent that, when combined with other components of an end product, will not render the end product unfit for its intended consumer use.

Unless specified otherwise, all vapor pressures listed in this disclosure are the vapor pressure at 25° C. It is noted, however, that the HVPVOC and LVPVOC vapor pressures are specified at 20° C., in accordance with the convention established by the California Air Resources Board (CARB).

As used herein, the term "c log P" refers to the calculated n-octanol/water partition coefficient. Preferably, it is calculated by "Molecular Modeling Pro" software (version 6.0.6), available from Chem SW, Fairfield, Calif.

In the event that c log P values cannot be calculated using "Molecular Modeling Pro" software (version 6.0.6), c log P values can be calculated as disclosed in U.S. Pat. No. 6,869,923 at col. 3, 11. 18-38, which is hereby incorporated by reference in its entirety. As disclosed therein, c log P values can also be calculated by the "C log P" program, available from Daylight CIS. The "calculated log P" (c log P) can also be calculated by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each fragrance component, and takes into account the numbers and types of atoms, the atom connectivity, and chemical bonding.

As used herein, the term "electrical liquid air freshener device" refers to device or system that includes an electrical or battery source of energy. The term "electrical liquid air freshener device includes heated liquid wick systems, piezo-electrical spraying systems, electrospray devices and Venturi devices, as well as devices that are powered by solar or other alternative forms of energy.

As used herein, a fragrance composition evaporates in a controlled fashion when the evaporation rate, measured as weight of fragrance loss, per unit of time (e.g, 0.2-0.6 g/day) over a given time period (e.g., 30, 40 or 60 days) is relatively constant over the given time period. In one embodiment, the evaporation rate is relatively constant when the weight of fragrance loss per unit of time differs by less than t 5%, or ±10% or ±20% over the given time period.

As used herein, the term "fragrance components" refer to components that impart a generally hedonically pleasing fragrance and includes both low vapor pressure VOC potentiator compounds and non-low vapor pressure VOC potentiator compounds that act as fragrance ingredients. In one embodiment, fragrance components refer to fragrance and flavor materials listed in either Allured's Flavor and Fragrance materials 2004, published by Allured Publishing Inc., the IFRA (International Fragrance Research Association) database, and RIFM (Research Institute of Fragrance Materials) database, each of which and hereby incorporated by reference in their entirety.

Low Vapor Pressure VOCs

As noted above, as used herein, a "low vapor pressure VOCs" or "LVPVOC" refers to organic solvents or carriers that have a vapor pressure of less than (<) 0.1 mm Hg at 20° C. Low vapor pressure VOCs, such as DPMA, have not been recognized and widely used, if at all, in liquid electrical air fresheners. When low vapor pressure VOCs are employed in combination with a composition that includes at least one low vapor pressure VOC potentiator compound, the resulting fragrance composition achieves performance that meets or exceeds the performance of comparable formulations that contain higher vapor pressure VOCs that are subject to increasingly stringent environmental regulation. These formulas are advantageous in that they can be fragranced with a low and/or pleasant fragrance profile and have a good weight loss profile, as well as, low toxicity issues and none of the VOC problems associated with other carriers that are typically used in air care applications.

In one embodiment, a LVPVOC solvent includes only those solvents that are approved for use by the California Air Resources Board (CARB) as LVPVOC solvents. Thus, in this particular embodiment, a LVPVOC solvent is a CARB-compliant solvent, and excludes non-CARB-compliant solvents.

An example of a low pressure VOC is dipropylene glycol methyl ether acetate (DPMA), which is commercially available, for example, from Dow Chemical (Midland, Mich.) under the brand name Dowanol® DPMA. Its major isomer is represented by the structure below:

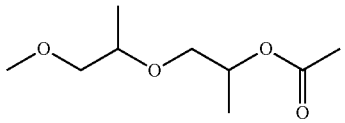

According to the vendor, Dowanol® DPMA has a vapor pressure of 0.08 mmHg at 20° C.

Other examples of low vapor pressure VOC solvents include, but are not limited to, Dowanol TPM, Dowanol DPNB and other VOCs with a VP less than 0.1 mmHg. The use of these solvents in conjunction with a low vapor pressure VOC potentiator compound yield formulations with the combined benefit of technical and hedonic performance that exceeds the performance that the low vapor pressure VOC and low vapor pressure VOC potentiator compound yield by themselves.

In one embodiment, the fragrance composition contains from about 1% to about 80%, from about 20% to about 60%, or from about 30% to about 50% by weight of LVPVOCs (e.g., DPMA), based on the total weight of the fragrance composition.

Low Vapor Pressure VOC Potentiator Compounds

Low vapor pressure VOC potentiator compounds can include certain fragrance materials selected from primary alcohols, secondary alcohols, aldehydes, esters, ketones, phenolic compounds and other recognized aromachemical compounds that meet the characteristics defined below. The non-VOC portion of the fragrance composition is constructed in such a way to achieve a higher than usual volatility, and is particularly well adapted for use in an electrical liquid electrical air freshener.

In one embodiment, low vapor pressure VOC potentiator compounds include, but are not limited to, hexyl acetate, 3,3,5-trimethylhexyl acetate, bornyl formate, 3-hexenyl butyrate, phenyl ethyl acetal, butyl hexanoate, isononanol, acetone alcohol, isoprenyl acetate, isobutyl 2-pentanoate, amyl propionate, herbal dioxane, furfuryl formate, methyl acetyl acetone, and butyl acetoacetate. In an alternative embodiment, the low vapor pressure VOC potentiator compounds are selected from the compounds listed in Table 1, below:

TABLE 1

Flash Point and Vapor Pressures (at 25° C.) of
Low Vapor Pressure VOC Potentiator Compounds

| Low Vapor Pressure VOC Potentiator Compound | CAS Number | Flash Point | Vapor Pressure |
|---|---|---|---|
| isopulegyl formate | 33522-69-9 | 190° F. | 0.1 mmHg |
| (Z)-7-decen-1-al | 10588-15-5 | 190° F. | 0.1 mmHg |
| ethyl benzoate | 94089-01-7 | 190° F. | 0.3 mmHg |
| (E)-2-decen-1-al | 101-97-3 | 190° F. | 0.1 mmHg |
| 4-isopropyl-2-cyclohexenone | 624-51-1 | 189° F. | 0.2 mmHg |
| methyl carbitol | 628-99-9 | 189° F. | 0.3 mmHg |
| butyl heptanoate | 4948-28-1 | 188° F. | 0.1 mmHg |
| 6-methyl-5-hepten-2-one propylene glycol acetal | 123-29-5 | 188° F. | 0.2 mmHg |
| phenyl acetaldehyde | 3913-81-3 | 188° F. | 0.4 mmHg |
| hexyl isothiocyanate | 111-87-5 | 187° F. | 0.1 mmHg |
| phenyl acetaldehyde dimethyl acetal | 5454-28-4 | 187° F. | 0.1 mmHg |
| decanal (aldehyde C-10) | 67452-27-1 | 186° F. | 0.1 mmHg |
| methyl nonanoate | 112-31-2 | 186° F. | 0.2 mmHg |
| verbenyl acetate | 53398-85-9 | 185° F. | 0.1 mmHg |
| sorbyl butyrate | 35154-45-1 | 185° F. | 0.1 mmHg |
| (E)-4-decen-1-al | 33467-79-7 | 185° F. | 0.1 mmHg |
| 2,3-butane diol | 72203-98-6 | 185° F. | 0.2 mmHg |
| (±)-menthone | 16930-93-1 | 185° F. | 0.3 mmHg |
| 4-decen-1-al | 59471-80-6 | 185° F. | 0.3 mmHg |
| verbenol | 21661-97-2 | 185° F. | 2.4 mmHg |
| tetrahydromyrcenyl acetate | 65405-70-1 | 184° F. | 0.2 mmHg |
| (E)-2-nonen-1-al | 4404-45-9 | 184° F. | 0.3 mmHg |
| isophorone | 54889-48-4 | 184° F. | 0.4 mmHg |
| ethyl acetoacetate | 101-48-4 | 184° F. | 0.8 mmHg |
| octanal propylene glycol acetal | 74094-61-4 | 183° F. | 0.1 mmHg |
| 2-nonen-1-al | 5009-32-5 | 183° F. | 0.3 mmHg |
| propylene glycol diacetate | 34300-94-2 | 183° F. | 0.6 mmHg |
| tetrahydrofurfuryl alcohol | 68258-95-7 | 183° F. | 0.8 mmHg |
| (Z)-3-hexen-1-yl 2-methyl butyrate | 78989-37-4 | 182° F. | 0.1 mmHg |
| (E)-isocitral | 53398-83-7 | 182° F. | 0.1 mmHg |
| isopropyl octanoate | 5458-59-3 | 181° F. | 0.2 mmHg |
| nonan-3-yl acetate | 60826-15-5 | 181° F. | 0.2 mmHg |
| methyl benzoate | 112-41-4 | 181° F. | 0.4 mmHg |
| 2-nonanol | 78-70-6 | 180° F. | 0.1 mmHg |
| tetrahydrocarvone | 6191-71-5 | 180° F. | 0.1 mmHg |
| propyl 2-furoate | 432-25-7 | 180° F. | 0.3 mmHg |
| acetophenone | 68480-08-0 | 179° F. | 0.4 mmHg |
| octanol | 6454-22-4 | 178° F. | 0.1 mmHg |
| (E)-3-nonen-2-one | 18492-65-4 | 178° F. | 0.3 mmHg |
| heptanal 2,3-butane diol acetal | 67859-96-5 | 177° F. | 0.2 mmHg |
| para-tolyl aldehyde | 97890-13-6 | 176° F. | 0.3 mmHg |
| (E)-2-hexen-1-yl 2-methyl butyrate | 1731-84-6 | 175° F. | 0.1 mmHg |
| 3-nonanol | 626-82-4 | 175° F. | 0.1 mmHg |
| (Z)-2-pinanol | 106-32-1 | 175° F. | 0.1 mmHg |
| (E,E)-2,4-heptadien-1-ol | 500-02-7 | 175° F. | 0.1 mmHg |
| ethyl (E)-4-octenoate | 147-89-91 | 175° F. | 0.2 mmHg |
| butyl hexanoate | 111-70-6 | 175° F. | 0.2 mmHg |
| 3-nonen-2-one | 103-09-3 | 175° F. | 0.8 mmHg |
| 3,3,5-trimethylhexyl acetate | 58430-94-7 | 174° F | 0.2 mmHg |
| (E,E)-2,4-octadien-1-al | 123-96-6 | 174° F. | 0.4 mmHg |
| linalool | 513-85-9 | 173° F. | 0.2 mmHg |
| ethyl phenyl acetate | 111-77-3 | 172° F. | 0.1 mmHg |
| 1-dodecene | 104-87-0 | 172° F. | 0.2 mmHg |
| isocyclocitral | 1335-66-6 | 172° F. | 0.3 mmHg |
| ortho-tolyl aldehyde | 2463-53-8 | 171° F. | 0.3 mmHg |
| ethyl nonanoate | 589-98-0 | 170° F. | 0.1 mmHg |
| beta-cyclocitral | 93-89-0 | 170° F. | 0.2 mmHg |
| homomenthyl acetate | 73757-27-4 | 170° F. | 0.2 mmHg |
| furfuryl acetone | 33467-76-4 | 170° F. | 0.3 mmHg |
| (E)-7-methyl-3-octen-2-one | 89-80-5 | 170° F. | 0.4 mmHg |
| citronellal | 106-23-0 | 169° F. | 0.3 mmHg |
| (S)-(−)-citronellal | 699-17-2 | 168° F. | 0.2 mmHg |
| diethyl oxalate | 18402-83-0 | 168° F. | 0.4 mmHg |
| 2-methyl butyl 3-methyl butenoate | 108-82-7 | 167° F. | 0.2 mmHg |

TABLE 1-continued

Flash Point and Vapor Pressures (at 25° C.) of
Low Vapor Pressure VOC Potentiator Compounds

| Low Vapor Pressure VOC Potentiator Compound | CAS Number | Flash Point | Vapor Pressure |
|---|---|---|---|
| ethyl octanoate | 18829-56-6 | 167° F. | 0.2 mmHg |
| dipropylene glycol methyl ether | 30390-50-2 | 166° F. | 0.6 mmHg |
| (Z)-4-hepten-1-ol | 74410-10-9 | 165° F. | 0.2 mmHg |
| heptanol | 70786-44-6 | 165° F. | 0.2 mmHg |
| heptanal cyclic propylene acetal | 529-20-4 | 165° F. | 0.4 mmHg |
| (E)-2-hepten-1-yl acetate | 615-10-1 | 165° F. | 0.5 mmHg |
| (3S,3aS,7aR)-dill ether | 89-54-87 | 164° F. | 0.3 mmHg |
| dill ether | 1125-88-8 | 164° F. | 0.3 mmHg |
| 5-methyl furfural | 20125-81-9 | 163° F. | 1.9 mmHg |
| (E)-2-hexen-1-yl butyrate | 4798-61-2 | 162° F. | 0.2 mmHg |
| 8-nonen-2-one | 30361-28-5 | 161° F. | 0.1 mmHg |
| (Z)-4-hepten-1-al diethyl acetal | 93-58-3 | 160° F. | 0.2 mmHg |
| isooctyl acetate | 122-78-1 | 160° F. | 0.2 mmHg |
| 2-octanol | 98-86-2 | 160° F. | 0.2 mmHg |
| (Z)-3-hepten-1-yl acetate | 1576-78-9 | 160° F. | 0.4 mmHg |
| 1-acetoxyacetone | 1120-21-4 | 160° F. | 3.3 mmHg |
| benzaldehyde dimethyl acetal | 95-92-1 | 157° F. | 0.4 mmHg |
| ethyl sorbate | 33046-81-0 | 157° F. | 0.5 mmHg |
| 2-octen-1-al | 50746-10-6 | 155° F. | 0.9 mmHg |
| amyl butyrate | 78-59-1 | 154° F. | 0.6 mmHg |
| heptyl acetate | 928-80-3 | 154° F. | 12.0 mmHg |
| 2,6-dimethyl-4-heptanol | 2396-84-1 | 151° F. | 0.3 mmHg |
| ethyl heptanoate | 67746-30-9 | 151° F. | 0.7 mmHg |
| butyl isothiocyanate | 73545-18-3 | 151° F. | 2.6 mmHg |
| 3-octanol | 16939-73-4 | 150° F. | 0.3 mmHg |
| (E)-2-hexen-1-al diethyl acetal | 34590-94-8 | 150° F. | 0.5 mmHg |
| methyl acetoacetate | 544-12-7 | 150° F. | 0.9 mmHg |
| hexanal propylene glycol acetal | 540-18-1 | 150° F. | 0.9 mmHg |
| ethyl 2-methyl-2-pentenoate | 623-84-7 | 150° F. | 1.4 mmHg |
| 3-mercapto-3-methyl butyl formate | 98-00-0 | 149° F. | 0.4 mmHg |
| furfuryl alcohol | 821-55-6 | 149° F. | 0.6 mmHg |
| 2-nonanone | 131671-56-2 | 148° F. | 0.6 mmHg |
| (±)-camphor | 76-22-2 | 148° F. | 0.7 mmHg |
| 2-heptanol | 106-30-9 | 148° F. | 1.2 mmHg |
| (E)-2-octen-4-ol | 30086-02-3 | 146° F. | 0.4 mmHg |
| 2-octen-4-ol | 141-97-9 | 146° F. | 0.4 mmHg |
| (E,E)-3,5-octadien-2-one | 14309-57-0 | 146° F. | 0.7 mmHg |
| 4-methyl-3-penten-1-ol | 97-99-4 | 146° F. | 1.000 mmHg |
| 3-mercapto-3-methyl butanol | 124-13-0 | 145° F. | 0.2 mmHg |
| 3-decanone | 2363-89-5 | 145° F. | 0.4 mmHg |
| 2,3,5-trithiahexane | 111-76-2 | 145° F. | 1.1 mmHg |
| benzaldehyde | 105-45-3 | 145° F. | 1.3 mmHg |
| 2-octanone | 928-94-9 | 145° F. | 1.4 mmHg |
| ethyl 2-hexenoate | 1599-49-1 | 144° F. | 1.3 mmHg |
| benzyl ethyl ether | 111-27-3 | 143° F. | 0.9 mmHg |
| beta-ocimene | 539-30-0 | 143° F. | 2.7 mmHg |
| (E)-4-hexen-1-ol | 928-92-7 | 142° F. | 0.9 mmHg |
| (Z)-3-hexen-1-yl isovalerate | 928-97-2 | 140° F. | 0.1 mmHg |
| undecane | 763-89-3 | 140° F. | 0.4 mmHg |
| (Z)-3-hexen-1-al diethyl acetal | 2311-46-8 | 140° F. | 0.5 mmHg |
| 2-butoxyethanol | 60415-61-4 | 140° F. | 0.9 mmHg |
| hexanol | 99-85-4 | 140° F. | 0.9 mmHg |
| (E)-3-hexen-1-yl acetate | 42474-44-2 | 140° F. | 1.2 mmHg |
| ethyl (E)-2-methyl-2-pentenoate | 3681-82-1 | 139° F. | 1.4 mmHg |
| 2-methyl-2-octen-1-al | 543-49-7 | 138° F. | 0.3 mmHg |
| (E)-3-hexen-1-ol | 1552-67-6 | 138° F. | 0.9 mmHg |
| sec-hexyl alcohol | 27829-72-7 | 137° F. | 1.5 mmHg |
| furfural | 100-52-7 | 137° F. | 2.2 mmHg |
| octanal diethyl acetal | 142-92-7 | 136° F. | 0.1 mmHg |
| 4-ethyl-6-hepten-3-one | 111-13-7 | 136° F. | 0.6 mmHg |
| (E)-2-hepten-1-ol | 58625-96-0 | 135° F. | 0.3 mmHg |
| 3-hexen-1-al | 1617-40-9 | 135° F. | 11.2 mmHg |
| 2-ethoxyethyl acetate | 3054-92-0 | 135° F. | 2.3 mmHg |
| isoprenyl acetate | 538-86-3 | 134° F. | 4.5 mmHg |
| acetone alcohol | 591-24-2 | 133° F. | 3.0 mmHg |
| amyl propionate | 97-95-0 | 133° F. | 3.6 mmHg |
| hexyl acetate | 64187-83-3 | 132° F. | 1.3 mmHg |
| 2-cyclohexenone | 106-73-0 | 132° F. | 3.6 mmHg |
| ethyl 2-hydroxy-2-methyl butyrate | 123-66-0 | 131° F. | 0.5 mmHg |
| ethyl (E)-2-hexenoate | 626-89-1 | 131° F. | 1.3 mmHg |
| 3-hexen-1-ol | 109-21-7 | 130° F. | 0.5 mmHg |
| (Z)-2-hexen-1-ol | 470-82-6 | 130° F. | 0.9 mmHg |
| benzyl methyl ether | 620-02-0 | 130° F. | 1.5 mmHg |
| ethyl (Z)-3-hexenoate | 105-30-6 | 130° F. | 1.6 mmHg |
| (E,E)-2,4-hexadien-1-al | 4440-65-7 | 130° F. | 4.8 mmHg |
| methyl heptanoate | 112-06-1 | 127° F. | 1.6 mmHg |
| valeraldehyde propylene glycol acetal | 626-77-7 | 127° F. | 2.3 mmHg |
| 2-pentyl butyrate | 71-41-0 | 126° F. | 1.1 mmHg |
| octanal (aldehyde C-8) | 98-01-1 | 125° F. | 0.9 mmHg |
| gamma-terpinene | 74094-60-3 | 125° F. | 1.1 mmHg |
| 3-methyl cyclohexanone | 111-15-9 | 125° F. | 1.5 mmHg |
| 4-methyl-1-pentanol | 473-67-6 | 125° F. | 1.7 mmHg |
| propyl hexanoate | 96-41-3 | 125° F. | 2.0 mmHg |
| cyclopentanol | 592-82-5 | 124° F. | 2.5 mmHg |
| 2-isohexyl alcohol | 13877-91-3 | 123° F. | 1.9 mmHg |
| 2,3,4-trimethyl-3-pentanol | 116-09-6 | 122° F. | 1.5 mmHg |
| 1,8-cineole | 35926-04-6 | 122° F. | 1.9 mmHg |
| ethyl hexanoate | 592-20-1 | 121° F. | 1.6 mmHg |
| butyl butyrate | 624-54-4 | 121° F. | 1.8 mmHg |
| isopropyl hexanoate | 930-68-7 | 120° F. | 1.0 mmHg |
| amyl alcohol | 97-64-3 | 120° F. | 2.2 mmHg |
| 1-hexen-3-yl acetate | 12-07-311 | 120° F. | 3.1 mmHg |
| ethyl lactate | 142-83-6 | 120° F. | 3.8 mmHg |
| 4-heptanone | 123-19-3 | 120° F. | 6.1 mmHg |

In one embodiment, the 3,3,5-trimethylhexyl acetate is obtained as Vanoris from IFF (New York, N.Y.).

Air Care Devices

Any one of the fragrance compositions disclosed herein can be used in any air care device, without limitation. The term "air care device" includes any suitable surface that allows for at least some evaporation of volatile materials. Any suitable air care device having any suitable size, shape, form, or configuration can be used. Suitable air care devices can be made from any suitable material, including but not limited to: natural materials, man-made materials, fibrous materials, non-fibrous materials, porous materials, non-porous materials, and combinations thereof. In certain embodiments, the air care devices used herein are flameless in character and include any device used for dispensing any type of volatile material (e.g. liquids) into the atmosphere (such as fragrance, deodorant, disinfectant or insecticide active agent). In certain non-limiting embodiments, a typical air care device utilizes a combination of a wick, gel, and/or porous surface, and an emanating region to dispense a volatile liquid from a liquid fluid reservoir.

Air care devices (such as, wicking devices) are known for dispensing volatile liquids into the atmosphere, such as fragrance, deodorant, disinfectant or insecticide active agent. A typical air care device utilizes a combination of a wick and emanating region to dispense a volatile liquid from a liquid fluid reservoir. Air care devices are described in U.S. Pat. Nos. 1,994,932; 2,597,195; 2,802,695; 2,804,291; 2,847,976. Ideally, the air care device should require little or no maintenance and should perform in a manner that allows the volatile material to be dispensed at a steady and controlled rate into the designated area while maintaining its emission integrity over the life span of the device.

In one embodiment, the air care device is an electrical liquid air freshener device. As noted above, the term "electrical liquid air freshener device" or "liquid electrical air freshener" refers to device or system that includes an electrical or battery operated source of energy which includes heated liquid wick delivery systems, piezoelectrical spraying systems, electrospray devices or Venturi devices. Commercial examples of electrical liquid air freshener devices include, but are not limited to, Glade® PlugIns® Scented oil, sold by SC Johnson & Sons; Air Wick Scented Oils, and Air Wick X-Press® Scented Oils, sold by Reckitt Benckiser; Febreze Noticeables sold by Proctor & Gamble Co., Electric Home Air Fresheners, sold by the Yankee Candle Co.; and Renuzit Scented Oils, sold by Henkel AG.

It has surprisingly been found that the combination of a low vapor pressure VOC (e.g., DPMA) and the fragrance composition can yield hedonically pleasing and constant fragrance profiles when used in an electrical liquid air freshener device. Thus, one embodiment of the presently disclosed subject matter provides an electrical liquid air freshener device that contains a fragrance composition disclosed herein.

The evaporation rate of the fragrance components(s) can be controlled to dispense the fragrance into the surrounding environment over extended periods of time. The perfumer of ordinary skill can modify the fragrance composition to provide controlled evaporation into small (e.g., a bath or living room) or large areas (e.g., large commercial and recreational spaces). In one embodiment, the presently disclosed fragrance compositions evaporate in a controlled fashion. A fragrance composition evaporates in a controlled fashion when the evaporation rate, measured as weight of fragrance loss, per unit of time (e.g, 0.2-0.6 g/day) over a given time period (e.g., 30, 40 or 60 days) is relatively constant over the given time period. In one embodiment, the evaporation rate is relatively constant when the weight of fragrance loss per unit of time differs by less than ±5%, or ±10% or +20% over the given time period.

In one embodiment, the presently disclosed fragrance compositions evaporate at a rate of from about 0.2 to about 0.6 grams per day, over 30, 40 or 60 days. In a still further embodiment, the evaporation rate (e.g., grams of fragrance lost per day), over a given time period (30, 40 or 60 days for example) varies by less than ±5%, or ±10%/a or ±20% over the given time period.

The use of a low vapor pressure VOC, as a carrier, and fragrance compositions of the present application is applicable to a wide variety of products in the fragrance industry including, but not limited to, electrical liquid air freshener devices. Suitable electrical liquid air freshener devices include in wick type air freshener devices, which may be fan assisted, piezoelectrical devices, as well as, other devices commonly used in the air care arena. A particularly preferred air care device that can be used with the fragrance compositions and low vapor pressure VOC solvents of the present application is disclosed in International Published Application No. WO 2009/006582 and U.S. Design Pat. Nos. D597,191 and D608,879. Each of these references are hereby incorporated by reference in their entirety.

Fragrance Components and Fragrance Compositions

The fragrance components that can be used in the fragrance compositions of the present disclosure include commercially available fragrances, preferably, but not limited to, fragrances available from Takasago International Corporation, (Tokyo, JP). Other sources of liquid or gel fragrance components include S.C. Johnson Company (Racine, Wis.), Procter & Gamble (Cincinnati, Ohio), Reckitt Benckiser (Berkshire, UK), Givaudan (Geneva, Switzerland), Firmenich (Geneva, Switzerland), and International Flavors and Fragrances (New York, N.Y.).

In one embodiment, the fragrance composition contains fragrance components (including both low vapor pressure VOC potentiator compounds and standard fragrance materials) in which at least about 5% to about 60% by weight, of the fragrance components have a clog P value greater than 3, more preferably at least about 10% to about 50%, by weight, of the fragrance components have a clog P value greater than 3 and most preferably at least about 20% to about 40%, by weight, of the fragrance components have a clog P value greater than 3, based on the total weight of the fragrance components present in the fragrance composition.

In one embodiment, the total amount of fragrance components is from about 20% to about 99% by weight, of the total weight of the fragrance composition (including any LVPVOCs and HVPVOCs). Alternatively, the total amount of fragrance components is from about 40% to about 80% by weight, or from about 50% to about 70% by weight, of the total fragrance composition (including any LVPVOC and HVPVOCs).

In one embodiment, from about 40 to about 95 weight percent of the fragrance components, based on the total weight of the fragrance components present in the fragrance composition, have a vapor pressure greater than 0.08 mmHg at 25° C. In alternative embodiments, from about 50 to about 85 weight percent of the fragrance components, or from about 60 to about 75 weight percent of the fragrance components, based on the total weight of the fragrance components present in the fragrance composition, have a vapor pressure greater than 0.08 mmHg at 25° C.

In one embodiment, from about 10 to about 40 weight percent of the total fragrance components have a boiling point of greater than or equal to about 250° C., based on the total weight of the fragrance components present in the fragrance composition. In an alternative embodiment, from about 10 to about 20 weight percent, or to about 30 weight percent of the total fragrance components have a boiling point of greater than or equal to about 250° C., based on the total weight of the fragrance components present in the fragrance composition.

The presently disclosed compositions can be in the form of a simple mixture of liquid fragrance components and LVPVOC solvents, or can be in an encapsulated form, e.g., entrapped in a solid matrix that may include wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, malitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Encapsulation techniques are well-known to persons skilled in the art, and may be performed, for instance, using techniques such as spray-drying, agglomeration or extrusion, or coating encapsulation, including coacervation and complex coacervation techniques.

EXAMPLES

The present application is further described by means of the examples, presented below, wherein the abbreviations have the usual meaning in the art.

Example 1

A commercially-available fruity fragrance composition is provided with the components shown below in Table 2 as Comparative Formulation A. This formulation contains greater than 50 wt % Dowanol DPM Glycol Ether and methoxy methyl butanol, which are VOCs that may not comply with the strictest environmental regulations, such as the regulations established by the California Air Resource Board (CARB).

A formulation with a similar evaporation rate, and olfactive properties as Comparative Formulation A is desired, yet using a low vapor pressure VOC solvent that complies with the strictest regulatory standards, (e.g., is CARB compliant). LOW VOC Carrier Formulation A' is provided that employs Dowanol DMPA (a LVPVOC), instead of Dowanol DPM Glycol Ether and methoxy methyl butanol. Formulation A' employs 3,5,5-trimethyl hexyl acetate and hexyl acetate as potentiator compounds.

TABLE 2

Fragrance Composition A and A'

| Component | CAS Number | Comparative Formulation A Weight Parts Per Thousand | LOW VOC Carrier Formulation A' Weight Parts Per Thousand |
|---|---|---|---|
| 1-HEXANOL, 3,5,5-TRIMETHYL-, ACETATE | 58430-94-7 | 314.706 | 403.943 |
| DOWANOL DPMA | 88917-22-0 | | 300.000 |
| 1-BUTANOL, 3-METHOXY-3-METHYL- | 56539-66-3 | 366.451 | |
| Oxiranecarboxylic acid, 3-methyl-3-phenyl-, ethyl ester | 77-83-8 | 70.588 | 70.588 |
| PROPANOL, 1(OR 2)-(2-METHOXYMETHYLETHOXY)- | 34590-94-8 | 32.785 | |
| 1,6-Octadien-3-ol, 3,7-dimethyl- | 78-70-6 | 32.353 | 32.353 |
| 4H-PYRAN-4-ONE, 3-ETHYL-3-HYDROXY- | 4940-11-8 | 16.471 | 16.471 |
| CYCLOHEXANOL, 4-(1,1-DIMETHYLETHYL)-, ACETATE | 32210-23-4 | 14.706 | 14.706 |
| 3-Buten-2-one, 4-(2,6,6-trimethyl-2-cyclohexen-1-yl)-, (E)- | 127-41-3 | 14.706 | 14.706 |
| Acetic acid, hexyl ester | 142-92-7 | | 10.000 |
| Acetic acid, phenylmethyl ester | 140-11-4 | 9.318 | 9.318 |
| Butanoic acid, ethyl ester | 105-54-4 | 8.824 | 8.824 |
| 2-BUTANONE, 4-(4-HYDROXYPHENYL)- | 5471-51-2 | 8.824 | 8.824 |
| 3-CYCLOHEXENE-1-CARBOXALDEHYDE, 3,6-DIMETHYL- | 67801-65-4 | 8.000 | 8.000 |
| Benzaldehyde, 4-hydroxy-3-methoxy- | 121-33-5 | 7.647 | 7.647 |
| Benzoic acid, 2-(methylamino)-, methyl ester | 85-91-6 | 5.882 | 5.882 |
| Ethanone, 1-(5,6,7,8-tetrahydro-2-naphthalenyl)- | 774-55-0 | 5.882 | 5.882 |
| BUTANOIC ACID, 2-METHYL-, 1-METHYLETHYL ESTER | 66576-71-4 | 4.941 | 4.941 |
| BUTANOIC ACID, 1,1-DIMETHYL-2-PHENYLETHYL ESTER | 10094-34-5 | 4.706 | 4.706 |
| OILS, ORANGE, SWEET | 8008-57-9 | 4.706 | 4.706 |
| Benzenemethanol, 4-methoxy-, acetate | 104-21-2 | 4.118 | 4.118 |
| Benzaldehyde | 100-52-7 | 4.118 | 4.118 |
| Benzaldehyde, 3-ethoxy-4-hydroxy- | 121-32-4 | 3.824 | 3.824 |
| 3-Buten-2-one, 3-methyl-4-(2,6,6-trimethyl-2-cyclohexen-1-yl)- | 127-51-5 | 3.529 | 3.529 |
| 3-Hexen-1-ol, (Z)- | 928-96-1 | 3.529 | 3.529 |
| 2(3H)-Furanone, 5-heptyldihydro- | 104-67-6 | 3.529 | 3.529 |
| 2H-Pyran-2-one, 6-heptyltetrahydro- | 713-95-1 | 3.059 | 3.059 |
| 2-PENTENOIC ACID, 2-METHYL- | 3142-72-1 | 3.000 | 3.000 |
| 2(3H)-Furanone, 5-hexyldihydro- | 706-14-9 | 2.941 | 2.941 |
| Butanoic acid, 3-oxo-, ethyl ester | 141-97-9 | 2.941 | 2.941 |
| 1,2-Propanediol | 57-55-6 | 2.462 | 2.462 |
| 3-BUTEN-2-ONE, 4-(2,6,6-TRIMETHYL-1-CYCLOHEXEN-1-YL)- | 14901-07-6 | 2.353 | 2.353 |
| 4H-Pyran-4-one, 3-hydroxy-2-methyl- | 118-71-8 | 2.353 | 2.353 |
| Ethanone, 1-phenyl- | 98-86-2 | 2.353 | 2.353 |
| LIME OIL DIST NAT | N/A | 2.353 | 2.353 |
| METH LAITONE 10% TEC | N/A | 2.059 | 2.059 |
| 3-HEXEN-1-OL, ACETATE, (Z)- | 3681-71-8 | 1.765 | 1.765 |
| 2-Propenal, 3-phenyl- | 104-55-2 | 1.765 | 1.765 |
| Butanoic acid, 3-methyl-, 3-methylbutyl ester | 659-70-1 | 1.471 | 1.471 |
| 2-BUTEN-1-ONE, 1-(2,6,6-TRIMETHYL-1-CYCLOHEXEN-1-YL)-, (E)- | 23726-91-2 | 1.235 | 1.235 |
| CYCLOPENTANEACETIC ACID, 3-OXO-2-PENTYL-, METHYL ESTER | 24851-98-7 | 1.176 | 1.176 |

TABLE 2-continued

| | | Fragrance Composition A and A' | |
|---|---|---|---|
| Component | CAS Number | Comparative Formulation A Weight Parts Per Thousand | LOW VOC Carrier Formulation A' Weight Parts Per Thousand |
|---|---|---|---|
| Benzenepropanal, 4-(1,1-dimethylethyl)-.alpha.-methyl- | 80-54-6 | 1.176 | 1.176 |
| Phenol, 2-methoxy-4-(2-propenyl)- | 97-53-0 | 1.176 | 1.176 |
| 2,4-CYCLOHEXADIENE-1-CARBOXYLIC ACID, 2,6,6-TRIMETHYL-, ETHY L ESTER | 35044-57-6 | 1.176 | 1.176 |
| 1% or less trace ingredients | | 9.042 | 9.042 |
| | | 1000.000 | 1000.000 |

Evaporation curves for Comparative Formulation A and Low VOC Carrier Formulation A' are shown in FIG. 1, measured as the amount of weight loss of the composition. As shown therein, evaporation of the Low VOC Carrier Formulation A' over 40 days is similar to that of Comparative Formulation A, which is not CARB compliant. Furthermore, a minimum of 4 of 5 expert "noses" selected Low VOC Carrier Formulation A' as an olfactive match to the non-compliant Comparative Formulation A.

Example 2

A commercially-available herbal fragrance composition is provided with the components shown below in Table 2 as Comparative Formulation B. This formulation contains greater than 50 wt % Dowanol DPM Glycol Ether and methoxy methyl butanol, which are VOCs that may not comply with the strictest environmental regulations, such as the regulations established by the California Air Resource Board (CARB).

A formulation with a similar evaporation rate, and olfactive properties as Comparative Formulation B is desired, yet using a low vapor pressure VOC solvent that complies with the strictest regulatory standards, (e.g., is CARB compliant). LOW VOC Carrier Formulation B' is provided that employs Dowanol DMPA (a LVPVOC), instead of Dowanol DPM Glycol Ether and methoxy methyl butanol. Formulation B' employs 3,5,5-trimethyl hexyl acetate as a potentiator compound.

TABLE 3

| | | Fragrance Composition B and B' | |
|---|---|---|---|
| Component | CAS Number | Comparative Formulation B Weight Parts Per Thousand | LOW VOC Carrier Formulation B' Weight Parts Per Thousand |
|---|---|---|---|
| DOWANOL DPMA | 88917-22-0 | | 440.984 |
| PROPANOL, 1(OR 2)-(2-METHOXYMETHYLETHOXY)- | 34590-94-8 | 307.062 | |
| 1-BUTANOL, 3-METHOXY-3-METHYL- | 56539-66-3 | 234.479 | |
| 1,6-Octadien-3-ol, 3,7-dimethyl-, acetate | 115-95-7 | 127.200 | 127.200 |
| 1-HEXANOL, 3,5,5-TRIMETHYL-, ACETATE | 58430-94-7 | 1.960 | 102.727 |
| 1,6-Octadien-3-ol, 3,7-dimethyl- | 78-70-6 | 84.265 | 84.114 |
| LAVANDIN GROSS | XUNK | 39.344 | 39.344 |
| Benzenemethanol, 4-methoxy-, acetate | 104-21-2 | 32.787 | 32.787 |
| 2(3H)-Furanone, dihydro-5-pentyl- | 104-61-0 | 18.057 | 18.057 |
| Benzaldehyde, 3-ethoxy-4-hydroxy- | 121-32-4 | 9.836 | 9.836 |
| METH LAITONE 10% TEC | N/A | 9.836 | 9.836 |
| Benzaldehyde, 4-hydroxy-3-methoxy- | 121-33-5 | 9.836 | 9.836 |
| 4H-PYRAN-4-ONE, 3-ETHYL-3-HYDROXY- | 4940-11-8 | 8.197 | 8.197 |
| BUTANOIC ACID, 1,1-DIMETHYL-2-PHENYLETHYL ESTER | 10094-34-5 | 7.311 | 7.311 |
| TERPENES AND TERPENOIDS, LEMON-OIL | 68917-33-9 | 5.255 | 5.255 |
| CYCLOHEXANEPROPANOIC ACID, 2-PROPENYL ESTER | 2705-87-5 | 4.918 | 4.918 |
| 3-CYCLOHEXENE-1-CARBOXALDEHYDE, 4-(4-HYDROXY-4-METHYLPENTYL)- | 31906-04-4 | 4.918 | 4.918 |
| Acetic acid, phenylmethyl ester | 140-11-4 | 4.754 | 4.754 |
| Hexanoic acid, 2-propenyl ester | 123-68-2 | 4.302 | 4.302 |
| 2H-Pyran-2-one, 6-heptyltetrahydro- | 713-95-1 | 3.934 | 3.934 |

TABLE 3-continued

| Fragrance Composition B and B' | | | |
|---|---|---|---|
| Component | CAS Number | Comparative Formulation B Weight Parts Per Thousand | LOW VOC Carrier Formulation B' Weight Parts Per Thousand |
| Benzaldehyde, 4-methoxy- | 123-11-5 | 3.444 | 3.444 |
| ETHANONE, 1-(1,2,3,4,5,6,7,8-OCTAHYDRO-2,3,8,8-TETRAMETHYL-2-NAPHTHALENYL)- | 54464-57-2 | 3.279 | 3.279 |
| Butanoic acid, ethyl ester | 105-54-4 | 3.279 | 3.279 |
| 1,4-Dioxacycloheptadecane-5,17-dione | 105-95-3 | 3.279 | 3.279 |
| LAVENDER OIL, SPIKE | 8016-78-2 | 3.279 | 3.279 |
| TERPENES AND TERPENOIDS, SWEET ORANGE-OIL | 68647-72-3 | 3.279 | 3.279 |
| OILS, CLARY SAGE | 8016-63-5 | 3.279 | 3.279 |
| 1,2-Propanediol | 57-55-6 | 3.167 | 3.167 |
| 3-Cyclohexene-1-methanol, .alpha.,.alpha.,4-trimethyl-, acetate | 80-26-2 | 3.050 | 3.050 |
| 2,6-Octadien-1-ol, 3,7-dimethyl-, (E)- | 106-24-1 | 2.951 | 2.951 |
| OILS, CEDARWOOD | 8000-27-9 | 2.843 | 2.843 |
| 7-OCTEN-2-OL, 2,6-DIMETHYL- | 18479-58-8 | 2.459 | 2.459 |
| Heptanoic acid, 2-propenyl ester | 142-19-8 | 2.033 | 2.033 |
| 2-BUTEN-1-OL, 2-ETHYL-4-(2,2,3-TRIMETHYL-3-CYCLOPENTEN-1-YL)- | 28219-61-6 | 1.967 | 1.967 |
| 2H-1-BENZOPYRAN-2-ONE, OCTAHYDRO- | 4430-31-3 | 1.967 | 1.967 |
| Propanoic acid, 2-methyl-, 2-phenoxyethyl ester | 103-60-6 | 1.967 | 1.967 |
| OILS, CEDARWOOD, TEXAN | 68990-83-0 | 1.884 | 1.884 |
| OILS, PATCHOULI | 8014-09-3 | 1.791 | 1.791 |
| 2(3H)-Furanone, 5-heptyldihydro- | 104-67-6 | 1.693 | 1.693 |
| CYCLOHEXANOL, 4-(1,1-DIMETHYLETHYL)-, ACETATE | 32210-23-4 | 1.658 | 1.658 |
| 1,3-Benzodioxole-5-carboxaldehyde | 120-57-0 | 1.640 | 1.640 |
| 2H-1-Benzopyran-2-one | 91-64-5 | 1.640 | 1.640 |
| Bicyclo2.2.1heptan-2-one, 1,7,7-trimethyl- | 76-22-2 | 1.639 | 1.639 |
| CYCLOPENTANEACETIC ACID, 3-OXO-2-PENTYL-, METHYL ESTER | 24851-98-7 | 1.311 | 1.311 |
| 6-OCTEN-1-OL, 3,7-DIMETHYL-, (S)- | 7540-51-4 | 1.311 | 1.311 |
| 3-Buten-2-one, 3-methyl-4-(2,6,6-trimethyl-2-cyclohexen-1-yl)- | 127-51-5 | 1.311 | 1.311 |
| OILS, ROSEMARY | 8000-25-7 | 1.206 | 1.206 |
| ETHANONE, 1-(5,6,7,8-TETRAHYDRO-3,5,5,6,8,8-HEXAMETHYL-2-NAPHTHALENYL)- | 21145-77-7 | 0.984 | 0.984 |
| BICYCLO[2.2.1]HEPTAN-2-OL, 1,3,3-TRIMETHYL- | 1632-73-1 | 0.984 | 0.984 |
| 1,3,4,6,7,8-HEXAHYDRO-4,6,6,7,8,8-HEXAMETHYLCYCLOPENTA-GAMMA-2-BENZOPYRAN | N/A | 0.984 | 0.984 |
| Butanoic acid, pentyl ester | 540-18-1 | 0.984 | 0.984 |
| 2H-Pyran-2-one, tetrahydro-6-pentyl- | 705-86-2 | 0.984 | 0.984 |
| Decanoic acid | 334-48-5 | 0.885 | 0.885 |
| PROPANOL, OXYBIS- | 25265-71-8 | 0.168 | 0.876 |
| Octanal, 7-hydroxy-3,7-dimethyl- | 107-75-5 | 0.820 | 0.820 |
| NAPHTHA (PETROLEUM), HYDROTREATED HEAVY | 64742-48-9 | 0.767 | |
| OILS, EUCALYPTUS | 8000-48-4 | 0.755 | 0.755 |
| 2(3H)-Furanone, 5-ethyldihydro- | 695-06-7 | 0.677 | 0.677 |
| Decanal | 112-31-2 | 0.656 | 0.656 |
| 1% or less trace ingredients | | 9.495 | 9.495 |
| | | 1000.000 | 1000.000 |

Figure 2:
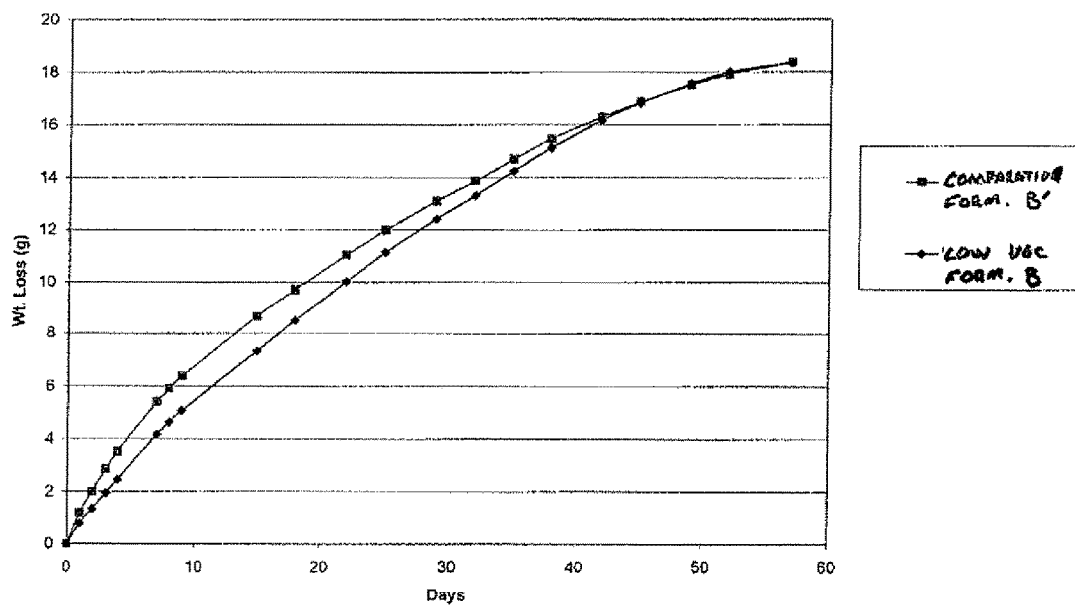
FIG. 2 is an evaporation comparison between the standard fragrance formulation B', and the Low Vapor Pressure VOC formulation B, as described in Example 2, measured as the amount of weight loss of fragrance over 40 days.

Evaporation curves for Comparative Formulation B and Low VOC Carrier Formulation B' are shown in FIG. 2, measured as the amount of weight loss of the composition. As shown therein, evaporation of the Low VOC Carrier Formulation B' over 40 days is similar to that of Comparative Formulation B, which is not CARB compliant. Furthermore, a minimum of 4 of 5 expert "noses" selected Low VOC Carrier Formulation B' as an olfactive match to the non-compliant Comparative Formulation B.

Example 3

A new fragrance that is CARB compliant formulation for use in an electrical liquid air freshener device. It achieves regulatory compliance and low VOC by preparing the formulation utilizing DPMA as a LVPVOC solvent or carrier. Dowanol DPNB and Dowanol TPM glycol ether have been previously utilized.

TABLE 4

Fragrance Composition C

| Component | CAS Number | LOW VOC Carrier Formulation C 1,000 Parts |
|---|---|---|
| DOWANOL DPMA | 88917-22-0 | 245.161 |
| 2-PROPANOL, 1-(2-BUTOXY-1-METHYLETHOXY)- | 29911-28-2 | 245.161 |
| PROPANOL, [2-(2-METHOXYMETHYLETHOXY) METHYLETHOXY]- | 25498-49-1 | 245.161 |
| 1-HEXANOL, 3,5,5-TRIMETHYL-, ACETATE | 58430-94-7 | 77.145 |
| ETHANONE, 1-(1,2,3,4,5,6,7,8-OCTAHYDRO-2,3,8,8-TETRAMETHYL-2-NAPHTHALENYL)- | 54464-57-2 | 62.903 |
| 2-BUTANOL, 1[[2-(1,1-DIMETHYL-ETHYL)CYCLOHEXYL]OXY]- | 139504-68-0 | 25.806 |
| 1,6-NONADIEN-3-OL, 3,7-DIMETHYL- | 10339-55-6 | 16.129 |
| 1H-3A,7-METHANOAZULENE, OCTAHYDRO-6-METHOXY-3,6,8,8-TETRAMET HYL-, [3R-(3.ALPHA., 3A.BETA.,6.BETA.,7.BETA.,8A.ALPHA.)]- | 19870-74-7 | 12.903 |
| 3-CYCLOPENTENE-1-BUTANOL, .ALPHA.,.BETA.,2,2,3-PENTAMETHYL- | 65113-99-7 | 7.742 |
| TERPENES AND TERPENOIDS, LEMON-OIL | 68917-33-9 | 6.606 |
| Benzenepropanal, 4-(1,1-dimethylethyl)-.alpha.-methyl- | 80-54-6 | 6.452 |
| Benzeneethanol | 60-12-8 | 6.452 |
| ACETIC ACID, ANHYDRIDE, REACTION PRODUCTS WITH BORON TRIFLUO RIDE AND 1,5,9-TRIMETHYL-1,5,9-CYCLODECATRIEVE | 144020-22-4 | 6.452 |
| 1,6-Octadien-3-ol, 3,7-dimethyl-, acetate | 115-95-7 | 5.342 |
| 2-BUTEN-1-OL, 2-METHYL-4-(2,2,3-TRIMETHYL-3-CYCLOPENTEN-1-YL)- | 28219-60-5 | 3.226 |
| CYCLOPENTANEACETIC ACID, 3-OXO-2-PENTYL-, METHYL ESTER | 24851-98-7 | 3.226 |
| OIL, CHAMPACA | 8016-23-7 | 2.581 |
| 1,4-DIOXACYCLOHEXADECANE-5,16-DIONE | 54982-83-1 | 2.581 |
| 1,6-Octadien-3-ol, 3,7-dimethyl- | 78-70-6 | 2.249 |
| OILS, MANILA ELEMI | 8023-89-0 | 1.972 |
| 6-Octen-1-ol, 3,7-dimethyl- | 106-22-9 | 1.936 |
| 2H-1-Benzopyran-2-one | 91-64-5 | 1.613 |
| BENZENEPROPANAL, .ALPHA.-METHYL-4-(2-METHYLPROPYL)- | 6658-48-6 | 1.290 |
| 1% or less trace ingredients | | 9.911 |

Figure 3:
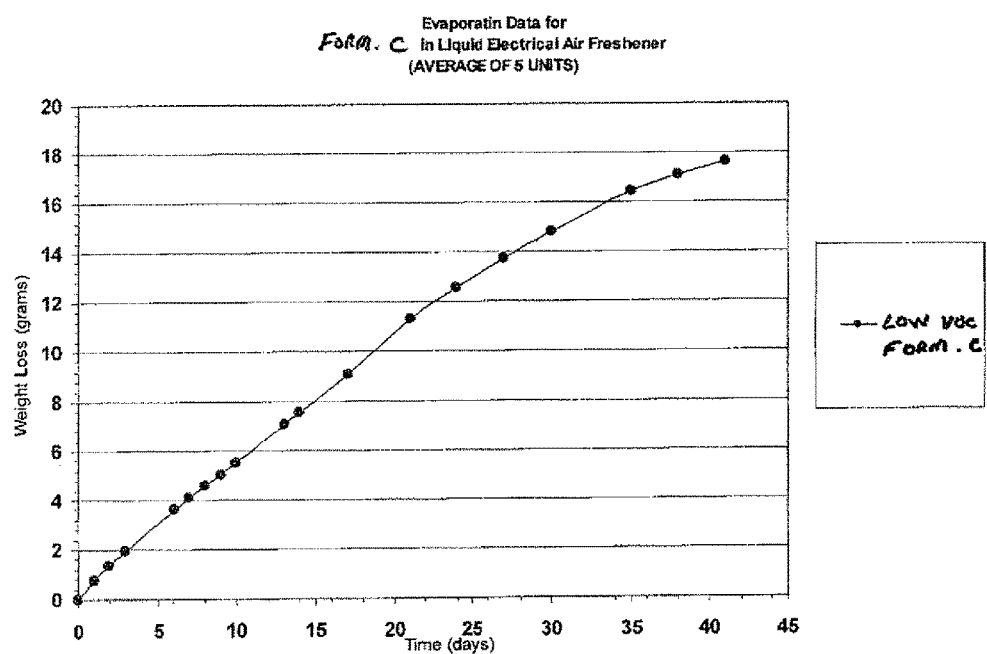
FIG. 3 is an evaporation curve for the fragrance formulation described in Example 3, measured as the amount of weight loss of fragrance over 40 days.

The evaporation curve of Low VOC Carrier Formulation C is shown in FIG. 3.

The use of such examples is illustrative only and in no way limits the scope and meaning of the invention or of any exemplified term or phrase used herein. Likewise, the invention is not limited to any particular preferred embodiments described herein. Indeed, many modifications and variations of the invention will be apparent to those skilled in the art upon reading this specification.

It is further to be understood that all values are approximate, and are provided for description.

Patents, patent applications, publications, product descriptions, and protocols are cited throughout this application, the disclosures of each of which is incorporated herein by reference in their entirety for all purposes.

What is claimed is:

1. An air care device comprising a fragrance composition wherein the fragrance composition comprises:
   a low vapor pressure volatile organic compound (VOC) in an amount of from about 1% to about 80% by weight;
   at least one low vapor pressure VOC potentiator compound, wherein the potentiator compound has a flashpoint of from about 110° F. to about 200° F.;
   wherein the composition has a relatively constant evaporation rate when fragrance loss per unit of time differs by less than about 20% over a given time period; and
   wherein the air care device is a wicking device or an electrical device.

2. The air care device of claim 1, wherein the fragrance composition comprises at least 10 wt % of the least one low vapor pressure VOC potentiator compound.

3. The air care device of claim 1, wherein the fragrance composition comprises at least 20 wt % of the least one low vapor pressure VOC potentiator compound.

4. The air care device of claim 1, wherein the at least one low vapor pressure VOC potentiator compound is represented by the formula:

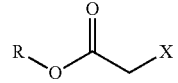

wherein
R is a $C_1$-$C_{10}$ substituted or unsubstituted alkyl, alkenyl group, or a $C_4$-$C_8$ substituted or unsubstituted cycloalkyl or aryl group; and
X is hydrogen, or a $C_1$-$C_5$ unsubstituted alkyl group.

5. The air care device of claim 4, wherein R is a $C_4$-$C_8$ substituted or unsubstituted alkyl group.

6. The air care device of claim 4, wherein R is substituted with one or more methyl groups.

7. The air care device of claim 1, wherein at least 80% of the fragrance composition evaporates within 30 days of being maintained at ambient conditions.

8. The air care device of claim 1, wherein the composition has a relatively constant evaporation rate when fragrance loss per unit of time differs by less than about 10% over a given time period.

9. The air care device of claim 1, wherein the composition has a relatively constant evaporation rate when fragrance loss per unit of time differs by less than about 5% over a given time period.

10. The air care device of claim 1, wherein the air care device is an electrical liquid air freshener.

11. The air care device of claim 1, wherein from about 10% to about 40% by weight of the compounds in the fragrance composition have a boiling point greater than or equal to about 250° C.

* * * * *